(12) United States Patent
McDermid (10) Patent No.: US 7,474,105 B2
(45) Date of Patent: Jan. 6, 2009

(54) SOIL MOISTURE SENSOR SYSTEMS AND METHODS

(75) Inventor: John McDermid, Loveland, CO (US)

(73) Assignee: Colorado Vnet, LLC, Loveland, CO (US)

( * ) Notice: Subject to any disclaimer, the term of this patent is extended or adjusted under 35 U.S.C. 154(b) by 0 days.

(21) Appl. No.: 11/611,083

(22) Filed: Dec. 14, 2006

(65) Prior Publication Data

US 2007/0145984 A1    Jun. 28, 2007

Related U.S. Application Data

(60) Provisional application No. 60/751,330, filed on Dec. 16, 2005.

(51) Int. Cl.
*G01R 27/26* (2006.01)

(52) U.S. Cl. .................. 324/689; 324/664; 324/690

(58) Field of Classification Search ............... 324/689
See application file for complete search history.

(56) References Cited

U.S. PATENT DOCUMENTS

| | | | | |
|---|---|---|---|---|
| 3,710,244 | A * | 1/1973 | Rauchwerger | 324/689 |
| 3,824,460 | A * | 7/1974 | Gustafson | 324/689 |
| 4,137,931 | A * | 2/1979 | Hasenbeck | 324/689 |
| 4,399,404 | A * | 8/1983 | Resh | 324/689 |
| 4,657,039 | A * | 4/1987 | Bireley et al. | 137/78.3 |
| 4,683,904 | A * | 8/1987 | Iltis | 324/678 |
| 5,479,104 | A * | 12/1995 | Cambell | 324/690 |
| 5,546,974 | A * | 8/1996 | Bireley | 137/78.3 |
| 5,859,536 | A * | 1/1999 | Stockton | 324/690 |
| 6,437,582 | B1 * | 8/2002 | Rode et al. | 324/658 |
| 2004/0145379 | A1 * | 7/2004 | Buss | 324/664 |
| 2006/0114006 | A1 * | 6/2006 | Mohamed | 324/690 |
| 2006/0188616 | A1 * | 8/2006 | Pierce et al. | 426/231 |

OTHER PUBLICATIONS

"Comparison of Soil-Moisture Sensors Between Neutron Probe, Time-Domain Reflectometry and Capacitance Probe", Report of the FAO/IAEA Final Consultants Meeting, Austria, Mar. 2003.
Kelleners, et al., "Calibration of Capacitance Probe Sensors Using Electric Circuit Theory", Soil Sci. Soc. Am. J. 68:430-439 (2004), Soil Science Society of America, WI, USA.
Robinson, et al., "Considerations for Improving the Accuracy of Permittivity Measurement Using Time Domain Reflectometry . . . ", Soil Sci. Soc. Am. J. 67:62-70 (2003).

(Continued)

*Primary Examiner*—Timothy J Dole
(74) *Attorney, Agent, or Firm*—Peter B. Scull; Berenbaum, Weinshienk & Eason

(57) ABSTRACT

Soil moisture sensor systems and methods are disclosed. An exemplary soil moisture sensor system includes a sensor configured to receive soil between parallel plates. A capacitive measurement circuit is operatively associated with the parallel sensor. A processor receives input from the capacitive measurement circuit. The processor determines moisture content of the soil between the parallel plates of the sensor based on the flowing relationship:

$$C = \frac{LH}{d}\varepsilon_0\varepsilon_r$$

where L is the length of the sensor, H is the height of the sensor, and d is the separation between the parallel plates of the sensor.

19 Claims, 5 Drawing Sheets

OTHER PUBLICATIONS

Jones, et al., "Standardizing Characterization of Electromagnetic Water Content Sensors: Part I. Methodology", UT State Univ., Univ. of CT.

Blonquist Jr., et al., "Standardizing Characterization of Electromagnetic Water Content Sensors: Part II. Evaluation of Seven Sensing Systems," UT State Univ.

\* cited by examiner

SOIL MOISTURE SENSOR SYSTEMS AND METHODS

PRIORITY APPLICATION

This application claims priority to co-owned U.S. Provisional Patent Application Ser. No. 60/751,330 for "Soil Moisture Sensor" of John McDermid, filed Dec. 16, 2005, hereby incorporated herein for all that it discloses.

TECHNICAL FIELD

The described subject matter relates to sensors in general, and more particularly to soil moisture sensor systems and methods.

BACKGROUND

Water conservation is increasingly important. Water supplies are essentially constant and more people are using the same water every year. In the United States, a substantial portion of the water supply is used to maintain landscape (trees, grass, etc.). Irrigation studies show that much of the water applied to the landscape by prevalent irrigation methods is wasted. Excess water ends tip as surface run-off or seepage into the ground.

Water lost as such is rarely captured and reused. Instead, surface run-off typically requires erosion control measures and often impacts mosquito abatement efforts. Seepage into the ground may pollute ground water with fertilizer and pesticides Reducing water loss for a landscape is a complex process. Soil types hold varying amounts of water and not all of the water held by the soil is available to the landscape. Landscape has varying water needs depending on whether the landscape is full sun, partial sun, or shady locations. Air temperature and humidity also play roles in determining how much water the landscape needs. The ground slope may affect the amount of water to apply to the landscape.

Soil moisture sensors have been used in the past. However, these sensors have been too expensive and/or inaccurate due to the variations in soil properties (e.g., composition, chemistry, compaction and temperature).

Although a Soil Moisture Neutron Probe (SMNP) has been shown to be fairly accurate, the public typically will not accept the use of neutron sources in their yards. Documentation and disposal issues are also a concern. Relative permittivity measurements using either a TDR method or a capacitive method have also been shown to be an effective indicator of volumetric water content. However, both methods have drawbacks.

SUMMARY

An exemplary soil moisture sensor system comprises a sensor configured to receive soil between parallel plates. A capacitive measurement circuit is operatively associated with the parallel sensor. A processor receives input from the capacitive measurement circuit. The processor determines moisture content of the soil between the parallel plates of the sensor based on the following relationship:

$$C = \frac{LH}{d}\varepsilon_0\varepsilon_r$$

where L is the length of the sensor, H is the height of the sensor, and d is the separation between the parallel plates of the sensor.

An exemplary method of determining soil moisture content comprises: receiving soil between at least two plates, measuring capacitance of the soil using a sensor circuit, and determining moisture content of the soil using the measured capacitance of the soil and length, height, and separation between the at least two plates.

DETAILED DESCRIPTION

Irrigation control conserves the water supply and reduces or altogether eliminates the cost of mitigating additional burdens from run-off and or seepage. Exemplary embodiments described and claimed herein provide a soil moisture sensor which may implement improved, or even optimal irritation control.

Among other exemplary advantages, the soil moisture sensor:

Enables measurements to be taken at low frequencies where dielectric relaxation is minimal and less expensive circuits may be employed.

Enables capacitive measurements to be taken where the effects of ionic conduction may be reduced or altogether eliminated.

Uses fewer, smaller parts.

Reduces manufacture costs relative to other commercially available sensors.

Provides accurate, laboratory-quality measurements.

Figure 1:
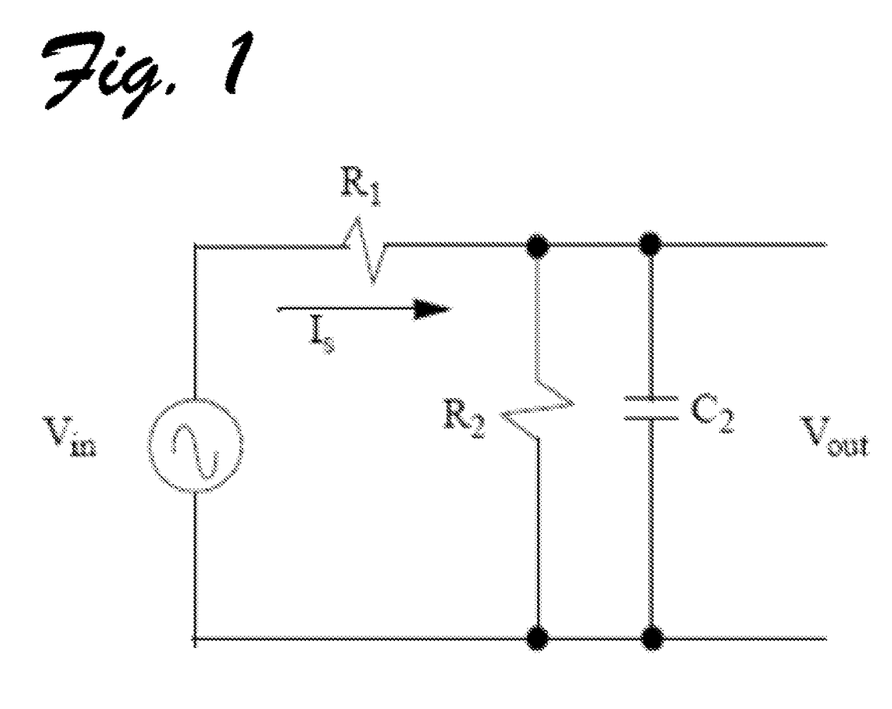
FIG. 1 is an exemplary capacitive measurement circuit that may be implemented for the soil moisture sensor.

In an exemplary embodiment, a sinusoidal voltage $V_1$ is applied to a capacitor through a resistor, $R_1$, as shown by the circuit 100 in FIG. 1.

The value $C_2$, which is indicative of the permittivity, is the value measured by the soil moisture sensor. The value $R_2$ represents the ionic conductivity of the medium. The voltage $V^{out}$ is a complex number having real and imaginary parts, as expressed by the following equation:

$$V_{out} = v_r + \iota v_t$$

where $\iota = \sqrt{-1}$

The capacitance may be determined from just the real and imaginary voltage measurements, the value of resistor $R_1$, and the radian frequency, as shown in more detail below in the section titled "exemplary calculations." The capacitance may then be expressed by the following equation:

$$C_2 = -\frac{V_{in}v_i}{\omega(v_r^2 + v_i^2)R_1}$$

Note that the capacitance value is independent of the value of ionic conductivity.

Figure 2:
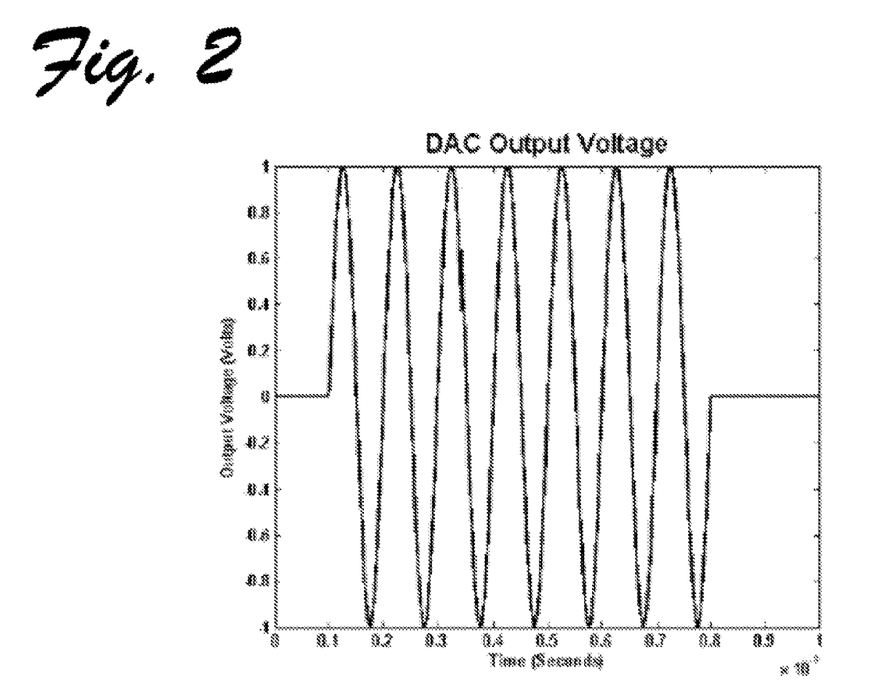
FIG. 2 shows exemplary DAC Output for the soil moisture sensor.
Figure 3:
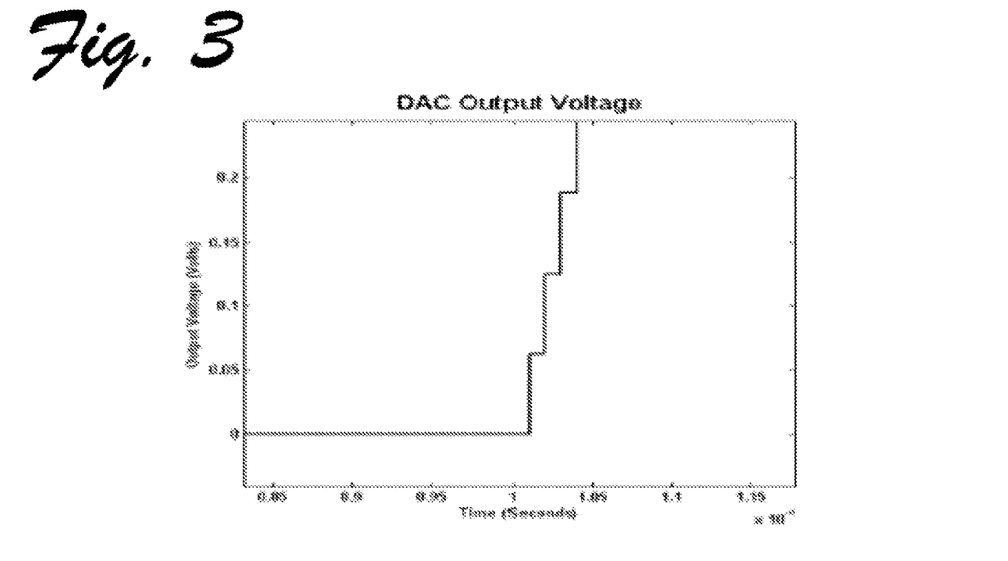
FIG. 3 is a ZOH view of the exemplary DACS Output shown in FIG. 3.

The circuit may be stimulated with a digital to analog converter (DAC) whose output is stepped through the values of a sin wave as shown by the plot 200 in FIG. 2. In this example, the DAC begins at zero and steps through seven complete cycles of the sin wave. The frequency of the sin wave is 10 KHz and the peak amplitude is 1 volt. The DAC output is a zero order hold (ZOH) output as shown by the plot 300 in FIG. 3.

Measurement starts with a sequence of A/D readings that are synchronized with the DAC. Sampling begins after some number of full cycles have been applied (two in this example). This delay allows any transient to settle to final value before the measurement begins.

Figure 4:
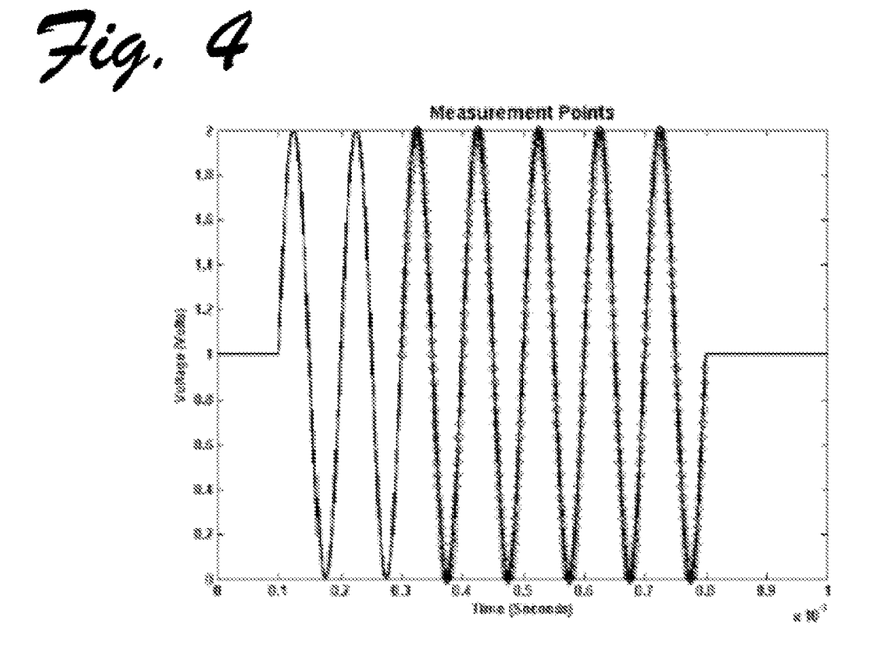
FIG. 4 are exemplary measurement points for the soil moisture sensor.

Measurement continues through all the remaining complete cycles of of the sin wave as shown by the plot 400 in FIG. 4. Each diamond marker indicates where a sample is taken.

Figure 5:
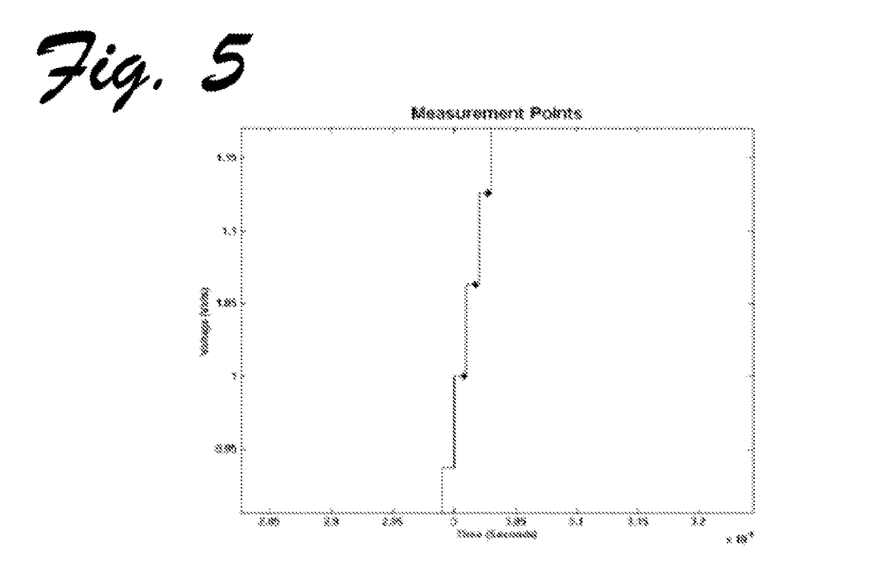
FIG. 5 is all expanded view of the exemplary measurement points shown in FIG. 4.

An expanded view of the samples is shown by the plot 500 in FIG. 5. Each measurement (diamond marker) is taken just prior to changing the DAC, allowing maximum settling time for the transient introduced by each step the DAC. Once the measurements have been collected, a digital Fourier transform provides the real and imaginary values. The digital Fourier transform is determined from the following equation, where N is the number of measurements taken:

$$v_r = \frac{\sqrt{2}}{N} \sum_{i=0}^{N-1} V_i \sin\left(\frac{2\pi k i}{N}\right)$$

$$v_i = \frac{\sqrt{2}}{N} \sum_{i=0}^{N-1} V_i \cos\left(\frac{2\pi k i}{N}\right)$$

A digital Fourier transform is computed for a discrete number of frequencies. The soil moisture sensor only needs the Fourier transform at the stimulation frequency. A particular frequency is determined by the integer k, the total number of samples N, the time between samples Δt. The integer k is chosen to correspond exactly with the stimulation frequency. That relationship is expressed by the following equation:

$$F = \frac{k}{N\Delta t}$$

The number of samples and the time between samples may be adjusted until this relationship is satisfied.

Figure 6:
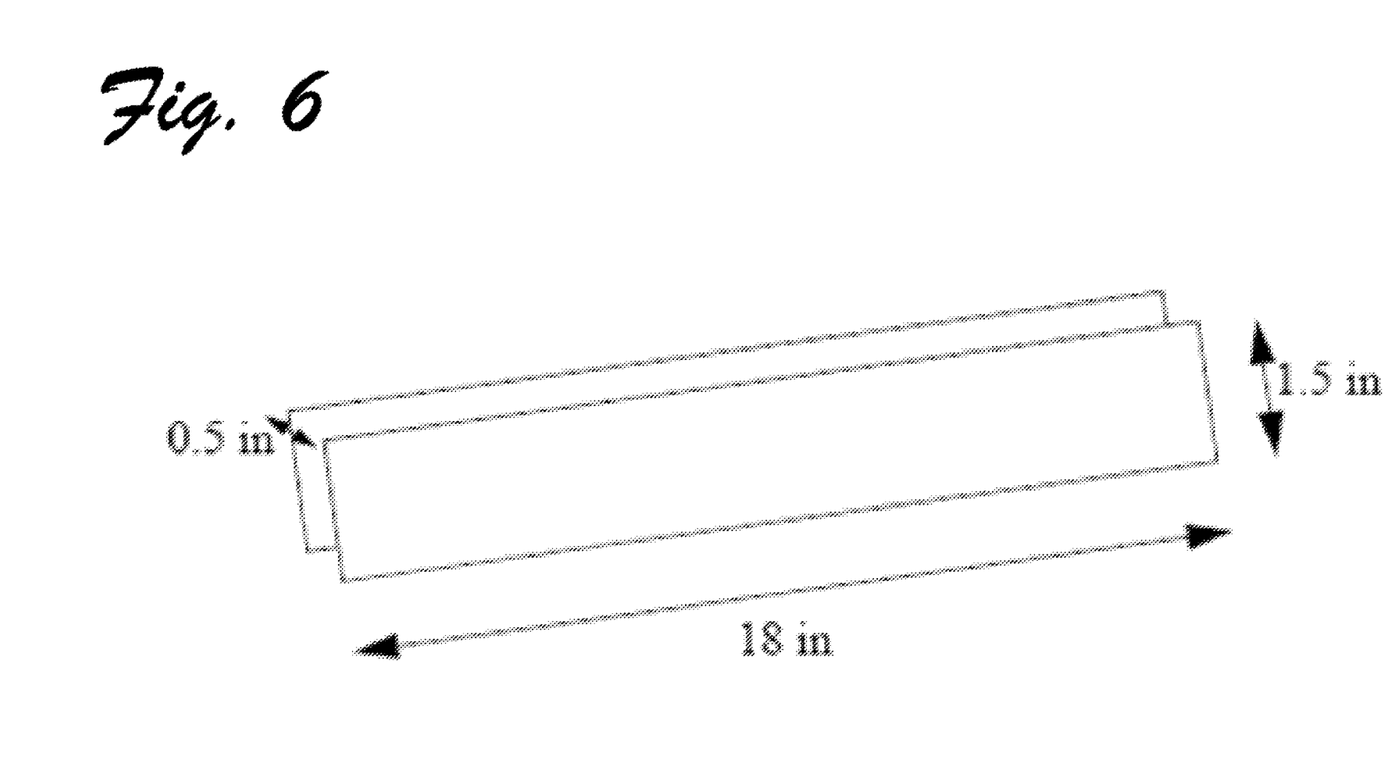
FIG. 6 is an exemplary moisture sensor as it may be implemented using substantially parallel plates.

It is noted that the capacitor geometry does not influence the measurement sensor other than the geometry should be known and remain constant. However, proper drainage of the soil should be maintained within the capacitor. In addition, the area between the plates should be easy to fill with soil. The form should also place the sensor in or near the root zone. A parallel plate capacitor, such as the exemplary soil moisture sensor 600 shown in FIG. 6, is a good choice to provide these characteristics.

For a parallel plate capacitor, the capacitance is expressed by the following equation, where L is the length of the sensor, H is the height of the sensor, and d is the separation between plates:

$$C = \frac{LH}{d}\varepsilon_0 \varepsilon_r$$

The value returned by the sensor may then be expressed by the following equation:

$$\varepsilon_r = \frac{d}{\varepsilon_0 LH}\left(\frac{V_{in}v_i}{\omega(v_r^2 + v_i^2)R_1}\right)$$

The 1.5 inch height of the soil moisture sensor helps keep the sensor at the root zone. The length and separation are sufficient to provide measurable capacitance. Of course other embodiments are also contemplated, as will be readily appreciated by those having ordinary skill in the art after becoming familiar with the teachings herein.

Figure 7:
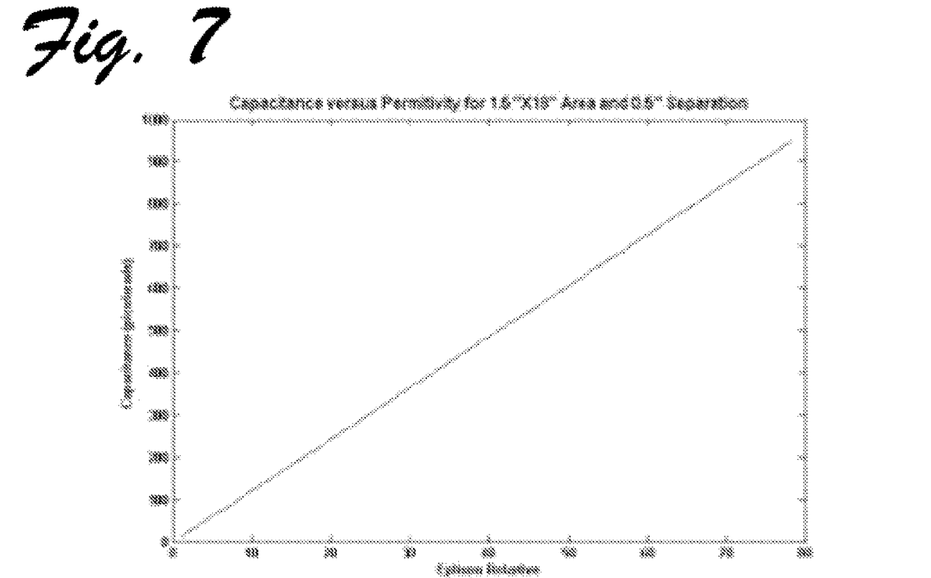
FIG. 7 shows exemplary capacitance as a function of relative permittivity.

The capacitance of the plates is shown by the plot 700 in FIG. 7. There is about 12 pF of capacitance between the plates in air and nearly 950 pF if the plates are immersed in water. This capacitance is within the measurement capabilities of a low cost processor that may be implemented for the soil moisture sensor, such as, but not limited to the Silicon Labs C8051F060X processor.

There are two calibrations for the soil moisture sensor. First, the permittivity of water is a function of temperature. That dependence is expressed by the following equation, where Tc is the temperature in degrees Centigrade.

$$\varepsilon_r = 78.54(1 - 4.579 \times 10^{-3}(T_c - 25) + 1.19 \times 10^{-5}(T_c - 25)^2 - 2.8 \times 10^{-8}(T_c - 25)^3)$$

Figure 8:
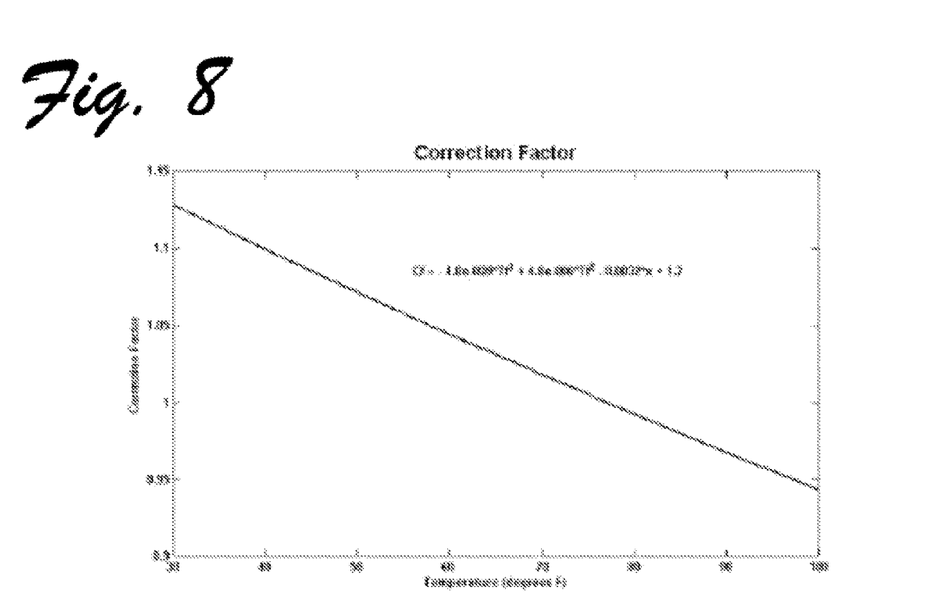
FIG. 8 shows an exemplary correction factor that may be implemented

A correction factor may be derived to correct the actual permittivity to the permittivity at 25° C. (77° F.). An exemplary correction factor is shown by the plot 800 in FIG. 8. The corrected permittivity may be calculated by dividing the measured permittivity by the correction factor. This factor may be applied to every measurement.

The second calibration is determined from a physical model and only needs to be done only in the design cycle. While the sensor is modeled as a parallel plate capacitor, physical construction details (e.g., spacers and fasteners) may modify the form factor slightly. Once a physical model has been assembled, the permittivity in air is measured. This permittivity becomes the correction factor and is stored in the measurement processor. A connected measurement is determined by dividing the actual measurement by the measured value in air.

Exemplary Calculations

As discussed above with reference to FIG. 1, the current through $R_1$ may be expressed by the following equation:

$$I_s = \frac{V_{in} - V_{out}}{R_1}$$

The complex voltage $V_{out}$ is expressed by the following equation:

$$V_{out} = \frac{R_2 \frac{1}{t\omega C_2}}{R_2 + \frac{1}{t\omega C_2}} I_s$$

$$= \frac{R_2}{t\omega C_2 R_2 + 1} I_s$$

$$= \frac{R_2}{t\omega C_2 R_2 + 1}\left(\frac{V_{in} - V_{out}}{R_1}\right)$$

Expanding and multiplying by the denominators results in the following equation:

$$V_{out}(t\omega C_2 R_2 + 1)R_1 = R_2(V_{in} - V_{out})$$

Multiplying out the right side and collecting terms containing $V_{out}$ is expressed by the following equation:

$$V_{out}(t\omega C_2 R_2 R_1 + R_1 + R_2) = R_2 V_{in}$$

Breaking $V_{out}$ into real and imaginary parts is expressed by the following equation:

$$V_{out} = v_r + t v_t$$

Substituting real and imaginary parts for $V_{out}$ is expressed by the following equation:

$$(v_r + t v_t)(t\omega C_2 R_2 R_1 + R_1 + R_2) = R_2 V_{in}$$

Multiplying out is expressed by the following equation:

$$t\omega C_2 R_2 R_1 v_r + R_1 v_r + R_2 v_r - 1\omega C_2 R_2 R_1 v_t + t R_1 v_t + t R_2 v_t = R_2 V_{in}$$

Equating the imaginary parts on both sides of the equation results in the following equation:

$$t\omega C_2 R_2 R_1 v_r + t R_1 v_t + t R_2 v_t = 0$$

Solving for the term $\omega C_2 R_2 R_1$ is expressed by the following equation:

$$\omega C_2 R_2 R_1 = \frac{-R_1 v_t - R_2 v_t}{v_r}$$

Now solving the equation for the real parts results in the following equation:

$$R_1 v_r + R_2 v_r - \omega C_2 R_2 R_1 v_t = R_2 V_{in}$$

Substituting for $\omega C_2 R_2 R_1$ from Equation 21 is shown by the following equation:

$$R_1 v_r + R_2 v_r - \left(\frac{-R_1 v_t - R_2 v_t}{v_r}\right) v_t = R_2 V_{in}$$

Simplifying is shown by the following equation:

$$R_1 v_r^2 + R_2 v_r^2 + R_1 v_t^2 + R_2 v_t^2 = R_2 V_{in} v_r$$

Solving for R2 is shown in the following equation:

$$R_2 = \frac{-R_1(v_r^2 + v_t^2)}{-V_{in} v_r + v_r^2 + v_t^2}$$

Solving Equation 21 for $C_2$ results in the following equation:

$$C_2 = \frac{-R_1 v_t - R_2 v_t}{\omega v_r R_2 R_1}$$

Substituting for $R_2$ results in the following equation:

$$C_2 = \frac{-R_1 v_t - \frac{-R_1(v_r^2 + v_t^2)}{-V_{in} v_r + v_r^2 + v_t^2} v_t}{\omega v_r \frac{-R_1(v_r^2 + v_t^2)}{-V_{in} v_r + v_r^2 + v_t^2} R_1}$$

Simplifying results in the following equation:

$$C_2 = -v_r R_1 \frac{V_{in} v_t}{\omega v_r (v_r^2 + v_t^2) R_1^2}$$

$$= \frac{V_{in} v_t}{\omega (v_r^2 + v_t^2) R_1}$$

In addition to the specific embodiments explicitly set forth herein, other aspects and implementations will be apparent to those skilled in the art from consideration of the specification disclosed herein. It is intended that the specification and illustrated embodiments be considered as examples only.

The invention claimed is:

1. A soil moisture sensor system comprising:
a sensor configured to receive soil between parallel plates;
a capacitive measurement circuit operatively associated with the sensor plates;
said capacitive measurement circuit comprising a stimulus portion and an analysis portion;
said stimulus portion generating a reference signal;
said analysis portion measuring the response from the sensor plates with respect to the reference signal in separate imaginary and real component measurements; and
using the response components measurements to compute a capacitance of the sensor plates based on known sensor plate geometry to derive a moisture measurement, wherein the known sensor plate geometry includes L as the length of the sensor, H as the height of the sensor, and d as the separation between the sensor plates and wherein moisture content of the soil is based on the following relationship: $C=(LH/d)\epsilon_0\epsilon_r$.

2. The system of claim 1 wherein the sensor is configured for positioning at root level.

3. The system of claim 1 wherein the capacitive measurement circuit is stimulated with a digital to analog converter (DAC) whose output is stepped through the values of a sin wave.

4. The system of claim 1 wherein capacitor geometry does not influence the sensor.

5. The system of claim 4 wherein the capacitor geometry is known and remains constant.

6. The system of claim 1 further comprising a drainage mechanism for the soil between the sensor plates.

7. The system of claim 1 wherein an area between the sensor plates is readily filled with soil.

8. The system of claim 1 wherein the sensor plates are arranged parallel to one another.

9. The system of claim 1 wherein the imaginary component measurement is reactive and the real component measurement is resistive.

10. A method of determining soil moisture content comprising:
    receiving soil between at least two plates;
    measuring capacitance of the soil using a capacitive measurement circuit operatively associated with the sensor plates;
    generating a reference signal from a stimulus portion of said circuit;
    measuring the response from the sensor plates with respect to the reference signal in separate imaginary and real component measurements; and
    using the response component measurements to compute a capacitance of the sensor plates based on known sensor plate geometry to derive a moisture measurement, wherein the known sensor plate geometry includes L as the length of the sensor, H as the height of the sensor, and d as the separation between the at least two plates, and wherein moisture content of the soil is based on the following relationship: $C=(LH/d)\epsilon_0\epsilon_r$.

11. The method of claim 10 wherein the sensor plates are arranged parallel to one another.

12. The method of claim 11 further comprising stimulating the capacitive measurement circuit by stepping output from a digital to analog converter (DAC) through a sin wave.

13. The method of claim 10 further comprising calibrating the sensor for temperature.

14. The method of claim 10 further comprising calibrating the sensor for a physical configuration of the plates.

15. The method of claim 14 wherein calibrating the sensor includes:
    measuring the permittivity in air; using the permittivity in air as a correction factor;
    determining a corrected soil moisture measurement by dividing an actual measurement of the sensor by the permittivity in air.

16. The method of claim 15 wherein calibrating the sensor further comprises storing the permittivity in air measurement for use with future measurements by the sensor.

17. A system for determining moisture content in soil comprising:
    plate means for receiving soil therebetween;
    sensor means for measuring capacitance of the soil;
    stimulus means for generating a reference signal;
    analysis means for measuring the response from the sensor means with respect to the reference signal in separate imaginary and real component measurements; and
    computational means for computing the capacitance of the sensor means based on known sensor plate geometry and deriving a moisture measurement, wherein the known sensor plate geometry includes L as the length of the plate means, H as the height of the plate means, and d as the separation between at least two plates of the sensor means, and wherein moisture content of the soil is based on the following relationship: $C=(LH/d)\epsilon_0\epsilon_r$.

18. The system of claim 17 further comprising means for calibrating the sensor means for temperature.

19. The system of claim 17 further comprising means for calibrating the sensor means for separation of the plate means.

\* \* \* \* \*